(12) United States Patent
Katz et al.

(10) Patent No.: US 9,933,307 B2
(45) Date of Patent: Apr. 3, 2018

(54) METHOD FOR DETECTING AND ANALZYING SURFACE FILMS

(71) Applicant: Orthobond, Inc., North Brunswick, NJ (US)

(72) Inventors: Jordan Katz, Short Hills, NJ (US); Abe Belkind, North Plainfield, NJ (US); Randy Clevenger, North Plainfield, NJ (US)

(73) Assignee: Orthobond, Inc., North Brunswick, NJ (US)

( * ) Notice: Subject to any disclaimer, the term of this patent is extended or adjusted under 35 U.S.C. 154(b) by 149 days.

(21) Appl. No.: 14/880,638

(22) Filed: Oct. 12, 2015

(65) Prior Publication Data

US 2016/0109358 A1   Apr. 21, 2016

Related U.S. Application Data

(60) Provisional application No. 62/062,379, filed on Oct. 10, 2014.

(51) Int. Cl.
*G01J 3/30* (2006.01)
*G01J 3/443* (2006.01)
*G01N 21/73* (2006.01)
*G01N 21/84* (2006.01)

(52) U.S. Cl.
CPC .............. *G01J 3/443* (2013.01); *G01N 21/73* (2013.01); *G01N 21/8422* (2013.01)

(58) Field of Classification Search
CPC ...... G01J 3/443; G01N 21/73; G01N 21/8422

USPC ......................................................... 356/316
See application file for complete search history.

(56) References Cited

U.S. PATENT DOCUMENTS

| | | | | |
|---|---|---|---|---|
| 5,128,007 A | * | 7/1992 | Matsunaga | G01N 21/8422 204/192.13 |
| 5,939,150 A | * | 8/1999 | Stelzle et al. | C23C 16/04 257/E21.232 |
| 6,633,391 B1 | * | 10/2003 | Oluseyi | G01N 21/71 356/630 |
| 2002/0124866 A1 | * | 9/2002 | Asari | C23C 16/345 134/1.1 |
| 2003/0090676 A1 | | 5/2003 | Goebel et al. | |
| 2004/0022960 A1 | | 2/2004 | Rhee et al. | |
| 2006/0261036 A1 | * | 11/2006 | Fazio | H01L 21/31116 216/59 |
| 2008/0123082 A1 | | 5/2008 | Luoh et al. | |
| 2012/0076922 A1 | | 3/2012 | Perret et al. | |
| 2013/0155404 A1 | | 6/2013 | Jeong et al. | |
| 2015/0032141 A1 | * | 1/2015 | Silvestro | A61B 17/3478 606/185 |
| 2015/0265339 A1 | * | 9/2015 | Lindquist | A61B 18/1492 606/41 |

OTHER PUBLICATIONS

International Search Report and Written Opinion for PCT Application No. PCT/US2015/055102 dated Jun. 30, 2016, 11 pages.

* cited by examiner

*Primary Examiner* — Hina F Ayub
(74) *Attorney, Agent, or Firm* — Lowenstein Sandler LLP

(57) ABSTRACT

Disclosed herein are embodiments of a novel method and system to analyze films using plasma to produce spectral data and analyzing the spectral data.

20 Claims, 6 Drawing Sheets

METHOD FOR DETECTING AND ANALZYING SURFACE FILMS

FIELD OF INVENTION

The present disclosure is directed to a method of analyzing films deposited onto a substrate by contacting the film with plasma to produce spectral data and analyzing the resulting spectral data. The method is useful in determining, e.g., the presence of a particular material on a substrate, the composition of the film, the amount of the material in the film, and the thickness of the film. The present disclosure is further directed to a system of analyzing films, wherein the film may be optionally deposited onto a substrate or absorbed onto the substrate.

BACKGROUND

The analysis of films is a major challenge in material science. This is especially the case when the films are deposited on a substrate. There exists a need in the art for a method and system of analyzing and quantifying films, such as, e.g., films that are deposited as a layer or a coating on a substrate.

OBJECTS AND SUMMARY OF THE INVENTION

It is an object of certain embodiments of the present invention to provide a method of analyzing a film by contacting the film with plasma to produce spectral data and analyzing the spectral data.

It is an object of certain embodiments of the present invention to provide a method of analyzing a film on a substrate by contacting the film with plasma to produce spectral lines and analyzing the spectral lines.

It is an object of certain embodiments of the present invention to provide a method of extricating surface materials with plasma and recording the spectral data of the resulting excitation of the extricated surface materials.

It is an object of certain embodiments of the present invention to provide a method of determining the composition of a film by fragmenting components of the film with a plasma comprising, e.g., argon, helium, hydrogen or oxygen, and analyzing the components.

It is an object of certain embodiments of the present invention to provide a method of detecting and analyzing molecular fragments (e.g., a fragment comprising C—N, P—O or other small organic fragments and combinations thereof) produced by exposure to plasma.

It is an object of certain embodiments of the present invention to provide a method of analyzing films deposited on a substrate using an optical emissions spectrometer.

It is an object of certain embodiments of the present invention to provide a method of analyzing the film deposited on a substrate made from, e.g., metal, semiconductor, glass, ceramic or other materials.

It is an object of certain embodiments of the present invention to provide a method of determining the composition of a film deposited on, e.g., medical devices, surgical devices and implants, drainage catheters, shunts, tapes, meshes, ropes, cables, wires, sutures, skin and tissue staples, burn sheets, external fixation devices, temporary/non-permanent implants, and other materials.

It is an object of certain embodiments of the present invention to provide a method of measuring the thickness of a film deposited onto a substrate or absorbed onto a substrate.

It is an objeion of certain embodiments of the present invention to provide a method of detecting the presence of an organic monolayer film.

It is an object of certain embodiments of the present invention to provide an analysis system for implementing the methods disclosed herein. In one embodiment, the system comprises a film, a plasma, and a spectral data recording device.

It is an object of certain embodiments of the present invention to provide a method of analyzing a film by that is simple and inexpensive.

BRIEF DESCRIPTION OF THE DRAWINGS

The above and other features of the present disclosure, their nature, and various advantages will become more apparent upon consideration of the following detailed description, taken in conjunction with the accompanying drawings, in which.

DETAILED DESCRIPTION

Figure 1:
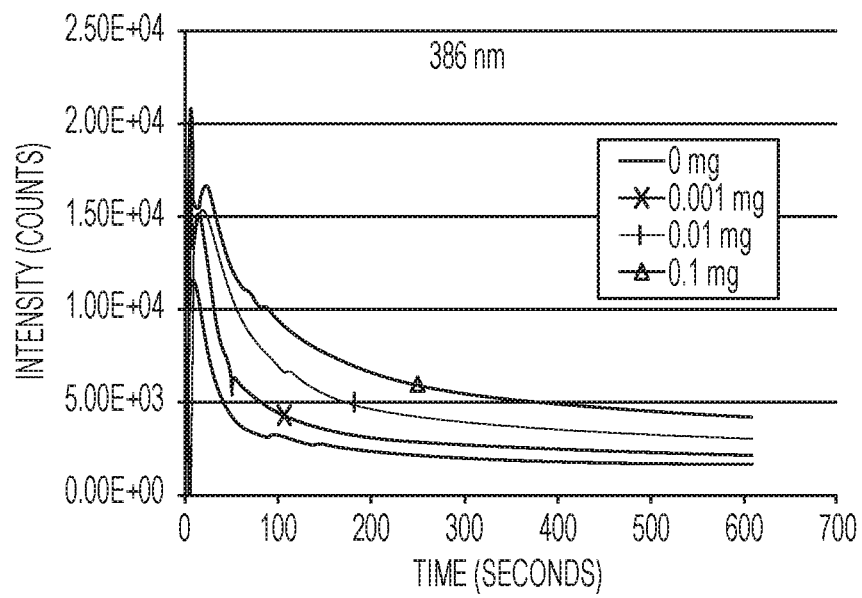
FIG. 1 is an intensity versus time chromatogram illustrating the relationship between the amount of material in a film and the area under the curve (AUC) obtained according to one embodiment of the invention.

As used herein, the term "area under the curve" refers to the area under the spectral line curve, or chart recorder function at a single wavelength over time, obtained from a device producing such data.

As used herein, the term "spectral data", refers to all the data obtained from a device producing such data, including and not limited to, an optical emission device. The data may include information generated directly or calculated downstream, including spectral lines, AUC, peak height, peak intensity, absorbance, peak width, models or correlations deduced from a pattern or trend obtained from the spectra and so on.

The present invention is directed to a method of analyzing films, comprising using plasma to produce spectral data and measuring the intensity of the transient spectral lines through optical emission spectroscopy. These emissions and resulting spectral data can be recorded over time and used to determine the amount, type, and composition of material present on a substrate's surface as well as the thickness of the film deposited onto the substrate. Recording and measuring all of the spectral lines present in the plasma assists in detecting the presence of specific elements such as nitrogen, phosphorus, chlorine, sodium and others, as well as the presence of molecular fragments such as any organic fragment (e.g., C—O, C—N, P—O and combinations thereof.

In some embodiments, the invention relates to a method for analyzing a film by contacting the film with plasma to produce spectral lines and analyzing the spectral lines. In certain embodiments, the film may be deposited on a substrate. This substrate may be made from a variety of materials, e.g., metal, semiconductor, glass or ceramic.

In other embodiments, the invention relates to a method comprising contacting the film with plasma, thereby removing one or more fragments from the film which produces some of the spectral lines. In certain embodiments, the materials from the film may be excited in the plasma. In some embodiments, the plasma may comprise, e.g., argon, helium, hydrogen or oxygen.

In some embodiments, the spectral data analysis is performed with an optical emissions spectrometer. In one embodiment, the spectrometer uses a fiber optic cable. In another embodiment, the spectrometer uses mirrors, lenses or any other tool designed to focus the light onto a detector. The spectral line, wavelength or other data produced by the film's exposure to plasma may be recorded over time. In one embodiment, the spectrometer measures the intensity of the spectral lines across time or across varying wavelengths.

In certain embodiments, analysis of the spectral data is used to determine the amount of material in the film. In one embodiment, the analysis is used to determine the composition of the film. In some embodiments, the analyzed data may be carbon-based. In some embodiments, the analysis determines the thickness of the film. In certain embodiments, the analysis determines the presence of an organic monolayer. In other embodiments, the analysis determines the presence of various elements in the film, such as, e.g., nitrogen, phosphorous, chlorine, sodium and combinations thereof. In still other embodiments, the analysis may determine the presence of a molecular fragment in the film, such as, e.g., fragments of C—N, P—O or combinations thereof.

In some embodiments, the method of analyzing a film comprises placing a film-coated substrate into a chamber; adding the plasma to the chamber; recording spectral data produced after addition of the plasma; and analyzing the spectral data.

In some embodiments, the method further comprises cleaning the chamber. Cleaning the chamber may occur before or after placing the substrate into the chamber. Cleaning may comprise filing the chamber with an inert gas where the inert gas may be argon. Another gas such as nitrogen can also be used. In certain embodiments, cleaning may occur at a pressure ranging from about 0.1 Torr to about 10 Torr, from about 0.1 Torr to about 5 Torr or at about 0.5 Torr. In other embodiments, cleaning may occur at a power ranging from about 1 Watt to about 1,000 Watts, from about 100 Watts to about 500 Watts or at about 200 Watts. In some embodiments, cleaning may occur for a period of time ranging from about 1 minute to about 60 minutes, from about 10 minutes to about 30 minutes or for about 20 minutes.

In certain embodiments, the cleaning comprises filling the chamber with argon gas at a pressure of 0.5 Torr and a power of 200 Watts for 20 minutes.

In some embodiment, the method comprises cleaning the chamber containing a film, contacting the chamber with plasma, recording spectral lines during the cleaning period, and analyzing the resultant spectral lines to identify the presence of contaminants, identity contaminants present in the film, and the amount or quantity of the contaminants.

In some embodiments, the chamber may be degassed. Degassing the chamber may occur before or after the film-coated substrate is placed therein, and in certain embodiments the degassing occurs after the substrate is placed in chamber. In some embodiments, degassing occurs at a pressure ranging from about 0.001 Torr to about 10 Torr, from about 0.1 Torr to about 1 Torr or at about 0.23 Torr.

After the chamber is degassed, in some embodiments the method further comprises flushing the chamber with an inert gas. In some of these embodiments, the inert gas may be, but not limited to, argon or nitrogen. In some embodiments, the flushing cycles may occur at a pressure ranging from about 0.001 Torr to about 10 Torr, about 0.005 Torr to about 5 Torr, from about 0.1 Torr to about 1 Torr or at about 0.5 Torr. In other embodiments, the flushing cycles may occur for a period of time ranging from about 1 minute to about 10 minutes, from about 1 minute to about 5 minutes or for about 3 minutes.

The degassing and flushing cycles may occur multiple times in some embodiments. In a particular embodiment, the degassing and flushing cycle occurs three times. In particular embodiments, the degassing and flushing cycles occur three times at 0.5 Torr for 3 minutes during each cycle. In certain embodiments, the degassing and flushing removes the atmospheric carbon and moisture from the chamber.

In some embodiments, after the degassing and flushing cycle(s), plasma is added. This plasma may be, but not limited to, argon, helium, hydrogen or oxygen plasma. In some embodiments, the plasma is added to a pressure ranging from about 0.1 Torr to about 10 Torr, from about 0.1 Torr to about 5 Torr or at about 0.5 Torr. In other embodiments, the plasma is added at a power ranging from about 1 Watt to about 1,000 Watts, from about 100 Watts to about 500 Watts or at about 200 Watts. Adding the plasma in other embodiments occurs for a period of time ranging from about 1 minute to about 60 minutes, from about 5 minutes to about 30 minutes or for about 10 minutes.

In certain embodiments, the plasma is added at a pressure of about 0.5 Torr and a power of about 200 Watts for about 10 minutes.

In some embodiments, data recorded from the method may be spectral data. This spectral data may be in the form of spectral lines. In some embodiments the spectral data is recorded with a spectrometer. In certain embodiments, the spectral data is recorded by an optical emission spectrometer. In certain embodiments, the spectrometer may record the spectral lines in a wavelength spectrum ranging from about 1 nm to 1 μm or from about 175 nm to about 950 nm. In other embodiments the spectral data is recorded at a rate ranging from about every 0.01 seconds to about every 1 second, about every 0.05 seconds to about every 0.5 seconds or about every 0.1 seconds. In still other embodiments, the spectral data is analyzed at a wavelength known to correspond to the fragments or particular elements present in the film.

In some embodiments, the thin film may be attached to the substrate through, e.g., covalent bonds, non-covalent bonds, chemical bonds, electrostatic interactions, ionic bonds, metallic bonds, hydrogen bonds, halogen bonds, Van der Waals forces, dipole-dipole interactions, dipole-induced dipole interactions, adsorption, painting, brushing, cross-linking, chemical vapor deposition, physical vapor deposition, epitaxy, electrodeposition, thermal deposition, evaporation, sputtering or casting.

Figure 3:
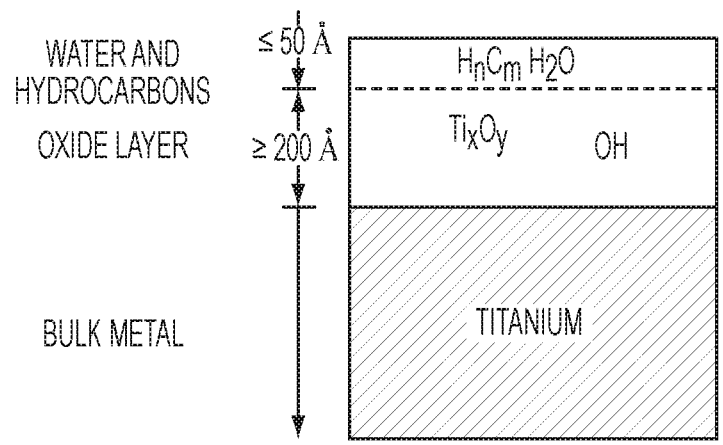
FIG. 3 illustrates a substrate having a film deposited thereon according to an embodiment of the invention.

The film to be used in this invention may consist of oxide, alkoxide, mixed oxide-alkoxide, phosphonate or organophosphonate in some embodiments. In other embodiments, the film is organic or inorganic, continuous or dispersed patterned, micropatterned or smooth, a monolayer or a multilayer, naturally occurring or intentionally deposited self-assembled layer(s). In certain embodiments, the film may be a self-assembled monolayer. In other embodiments, the film may be multilayered. In certain embodiments, as illustrated in FIG. 3, one layer may comprise oxide, alkoxide, mixed oxide-alkoxide, phosphonate, or organophosphonate, and a second layer may comprise water and hydrocarbons. In certain embodiments the layer comprising oxide, alkoxide, mixed oxide-alkoxide, phosphonate, or organophosphonate, may have a thickness greater the 0.02 µm. In certain embodiments the layer comprising water and hydrocarbons has a thickness smaller than 0.005 µm. In some embodiments, the invention is directed to cleaning contaminants from the layer comprising water and hydrocarbons, such that a thin film desired to be further analyzed remains.

In other embodiments, the method may be used where the thickness of the film ranged from about 0.001 µm to about 1 µm, from about 0.1 µm to about 0.5 µm, or from about 0.1 µm to about 0.3 µm. In certain embodiments, the method may be used where the film's thickness is 1 µm or less. In some embodiments, the method may be used were the film's thickness is 0.8 µm or less, 0.6 µm or less, 0.4 µm or less, 0.2 µm or less or 0.1 µm or less. In some particular embodiments, the method may be used with films having a thickness ranging from about 0.0001 µm to about 1 µm.

In other embodiments, the invention may be used to analyze films on different substrates including, but not limited to a metal, alloy, polymer, plastic, ceramic, silicon, glass, tissue or fabric.

In some embodiments, the substrate may be metal, such as, e.g., titanium, stainless steel, cobalt, chrome, nickel, molybdenum, tantalum, zirconium, magnesium, manganese, niobium, iron, gold, copper, aluminum, silver, platinum, vanadium, tin, palladium, iridium, antimony, bismuth, zinc, tungsten and alloys thereof.

In other embodiments, the substrate may be a polymer, which may be selected from the group consisting of, polyamides, polyurethanes, polyureas, polyesters, polyketones, polyimides, polysulfides, polysulfoxides, polysulfones, polythiophenes, polypyridines, polypyrroles, polyethers, silicones, polysiloxanes, polysaccharides, fluoropolymers, amides, imides, polypeptides, polyethylene, polystyrene, polypropylene, glass reinforced epoxies, liquid crystal polymers, thermoplastics, bismaleimide-triazine (BT) resins, benzocyclobutene polymers, Ajinomoto Buildup Films (ABF), low coefficient of thermal expansion (CTE), films of glass and epoxies, polyethylene terephthalate (PET), polyetheretherketones (PEEK), and polyetherketoneketones (PEKK) or combinations thereof. In certain embodiments, the polymer may be selected from the group consisting of polyethylene terephthalates (PET), polyetheretherketones (PEEK), or polyetherketoneketones (PEKK) and combinations thereof.

In other embodiments, the substrate may be a plastic. In some embodiments, the plastic may be selected from the group consisting of polyolefins, polyethylene/acrylate copolymers, polyacrylate homo and copolymers, phenoxy polymers, polystyrenes and copolymers, polyacetal (polyoxymethylene) homo and copolymers, polycarbonates, polyethylenes, naphthalates, polyamide/imides, polybenzimidazoles, synthetic rubbers, vinyl polymers, cellulose derivatives, polybutylenes, ethylene methyl acrylates, polyethylene terephthalates, polybutylene terephthalates, nylon 6, nylon 6,6, nylon 4,6, nylon 11, nylon 12, aramids, polymethylmethacrylates, sulfone, s epichlorohydrin/bisphenol resins, polyacrylonitrile/butadiene/styrenes (ABS), polyamide/imides, ethylene-chlorotrifluoroethylenes, ethylene/propylene/diene monomers (EPDM), chlorinated rubbers, nitro rubbers, styrene butadiene rubbers, polylactides, polyvinyl acetates and copolymers, polyvinyl butyrals, polyvinyl chlorides, cellulose acetate homopolymers and copolymers with cellulose propionate and cellulose butyrates, nitro celluloses and combinations thereof.

In other embodiments, the substrate may be a ceramic. In some embodiments, the ceramic may be calcium phosphates, calcium phosphate cements, biocompatible magnesium doped calcium phosphates, calcium carbonates, calcium sulfates, barium carbonates, barium sulfates, alphatricalcium phosphates (a-TCP), tricalcium phosphates (TCP), betatricalcium phosphates (β-TCP), hydroxyapatites (HA), biphasic calcium phosphates, biphasic composite between HA and β-TCP, aluminas, zirconias, bioglasses, biocompatible silicate glasses, biocompatible phosphate glasses and combinations thereof.

In other embodiments, the substrate may be a silicon, including but not limited to, amorphous silicons, undoped polysilicons, doped polysilicons, single crystal silicons, monocrystalline silicons, polycrystalline silicons, nanocrystalline silicons, porous silicons, polycrystalline silicons and combinations thereof.

In other embodiments, the substrate may be a glass, including but not limited to, silicate glasses, perlite glasses, zonalites glasses, fermiculite glasses, soda lime silicas, borosilicate glasses, aluminosilicate glasses, borate glasses, phosphate glasses, oxide glasses, halide glasses, sulfide glasses, chalcogenide glasses, pre-fused glasses, recycled glasses, manufactured glasses and combinations thereof.

In other embodiments, the substrate may be a tissue, including but not limited to, connective tissues, non-connective tissues, tendons tissues, ligament tissues, blood vessel tissues, arterial tissues, venous tissues, neural tissues, organ tissues, fascias, pericardial tissues, dermal tissues, adipose tissues, dura tissues, fibrous tissues, cartilage tissues, bone tissues, placental tissues, endothelial tissues, epithelial tissues, epidermal tissues, synovial membranes, muscle tissues, mucus membrane tissues and cardiac tissues.

In other embodiments, the substrate may be a fabric, including but not limited to, polyesters, nylons, acetates, acrylics, polycottons, cottons, cotton-polyester blends, silks, knits, wools, aramids, canvases, meshes, rayons, nonwovens, spun bonded, gauzes, cashmeres, wet laid nonwoven fabrics of polyolefins, nylons, rayons, cellulosic fibers and combinations thereof.

In some embodiments, the substrate may be a medical device, including but not limited to, an implantable or percutaneous medical device, endoscopic, arthroscopic, laproscopic, cardiac, cardiovascular, vascular medical device, orthopedic, orthopedic trauma, spine medical device, surgical devices, implants, drainage catheters, shunts, tapes, meshes, ropes, cables, wires, sutures, skin and tissue staples, burn sheets, external fixation devices or temporary/non-permanent implants.

In some embodiments, this invention is directed to a system for analyzing films comprising a film; a plasma; and a spectral data recording device. In other embodiments, the system for analyzing a film may comprise a substrate with a film; a chamber; plasma; and a spectral line recording device.

In certain embodiments, algorithms for the data analysis and device operation described herein may be executed by a computer system as described below. The computer system may operate in the capacity of a server or a client machine in client-server network environment, as a peer machine in a peer-to-peer (or distributed) network environment, or as a component of a laboratory or industrial-scale machine (e.g., a plasma chamber, spectrometer or characterization device). The computer system may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that computer system.

An exemplary computer system includes one or more of a processing device (processor), a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), or a data storage device, each of which may communicate with each other via a bus.

The processor may correspond to a general-purpose processing device such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. The processor may be configured to execute instructions for performing any algorithms useful for carrying out embodiments described herein.

The computer system may further include a network interface device. The computer system also may include a video display unit (e.g., a liquid crystal display (LCD), a cathode ray tube (CRT), or a touch screen), an alphanumeric input device (e.g., a keyboard), a cursor control device (e.g., a mouse), and a signal generation device (e.g., a speaker).

The data storage device may include a computer-readable storage medium on which is stored one or more sets of instructions (e.g., software) embodying any one or more of the methodologies or functions described herein. The instructions may also reside, completely or at least partially, within the main memory and/or within the processor during execution thereof by the computer system, the main memory and the processor also constituting computer-readable storage media. The instructions may further be transmitted or received over a network via the network interface device.

It is noted that the term "computer-readable storage medium" should be taken to include a single medium or multiple media (e.g., a centralized or distributed database, and/or associated caches and servers) that store the one or more sets of instructions. The term "computer-readable storage medium" shall also be taken to include any transitory or non-transitory medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

A power device may monitor a power level of a battery used to power the computer system or one or more of its components. The power device may provide one or more interfaces to provide an indication of a power level, a time window remaining prior to shutdown of computer system or one or more of its components, a power consumption rate, an indicator of whether computer system is utilizing an external power source or battery power, and other power related information. In some embodiments, indications related to the power device may be accessible remotely (e.g., accessible to a remote back-up management module via a network connection). In some embodiments, a battery utilized by the power device may be an uninterruptible power supply (UPS) local to or remote from computer system. In such embodiments, the power device may provide information about a power level of the UPS.

Some portions of the detailed description may be performed through execution of algorithms. Algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the preceding discussion, it is appreciated that throughout the description, discussions utilizing terms such as "generating", "quantifying", "analyzing" and "determining", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer- or machine-readable storage medium, such as, but not limited to, any type of disk including floppy disks, optical disks, compact disk read-only memories (CD-ROMs), and magnetic-optical disks, read-only memories (ROMs), random access memories (RAMs), EPROMs, EEPROMs, magnetic or optical cards, or any type of media suitable for storing electronic instructions.

The following is an example of a detailed analysis performed on a thin film deposited on titanium alloy substrate samples. It is set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLE 1

Samples of titanium alloy were thoroughly cleaned using a series of detergent washes followed by sonication in water and ethanol. Control samples were set aside in clean glass containers for subsequent analysis. A stock solution of MDPB (methacryloyloxydodecylpyridinium bromide) was prepared in deionized water at a concentration of 1 mg/ml. A 10× dilution series was performed from the stock solution and 100 µl of the stock and each of two dilutions was pipetted onto clean titanium alloy samples so that the following amounts of MDPB were present on the series of samples: 0.1 mg, 0.01 mg and 0.001 mg.

In addition, a sample was prepared with 100 µl of water so that it could be used as a control.

All of the titanium alloy samples were then placed in an oven set at a temperature of 120° C. to evaporate the water leaving a thin film of MDPB on the surface. The coupons were aged in the oven for 30 minutes to allow for exhaustive removal of moisture from the surface.

An Autoglow (Glow Research) plasma chamber with an integrated fiber optic cable connected to a QE Pro Spectrometer (Ocean Optics) was used for cleaning and spectral analysis. Prior to testing the titanium alloy samples, the quartz chamber of the Autoglow was cleaned using argon gas at a pressure of 0.5 Torr and a power of 200 Watts for 20 minutes. After the chamber was cleaned, the samples were each tested using the following procedure.

A single coupon was placed in the center of the chamber and the chamber was vacuum degassed to a pressure of 0.23 Torr. Next the chamber was flushed with argon gas for three minutes at a pressure of 0.5 Torr. This vacuum/purge cycle was repeated two additional times in order to exhaustively remove atmospheric carbon contamination and any remaining moisture.

Following the vacuum/purge cycles, an argon plasma at 0.5 Torr and 200 Watts was struck for 10 minutes. Immediately upon establishing the plasma, the spectrometer was set to record the entire spectrum from 175 nm to 950 nm every 0.1 seconds for the duration of the plasma treatment.

The flushing and degassing cycle was repeated for each sample, followed by a plasma treatment and similar optical emission spectrometry analysis. Between each sample analysis the chamber was cooled down for 10 minutes under vacuum.

The spectral data was analyzed. Spectral data in several wavelengths showed a relationship or correlation between peak height and the starting MDPB concentration. From all wavelengths showing a correlation between peak height and the starting MDPB concentration, a wavelength of 386 nm was selected for detailed analysis. A wavelength of 386 nm is known to correspond to C—N fragments, thereby assisting in detecting the type of material (e.g., elements or fragments) in the film.

Once a wavelength for detailed analysis was selected, a chart recorder analysis was implemented to track the peak height at 386 nm as a function of time. The resulting chromatogram is shown in FIG. 1 below. It is apparent that there is a dose dependent relationship between MDPB concentration and area under these curves. A sample with a higher starting concentration results in a higher material dose or amount deposited on the substrate, thereby resulting in a higher peak, a wider peak, and a greater area under the curve as compared to samples with lower starting concentration.

Figure 2:
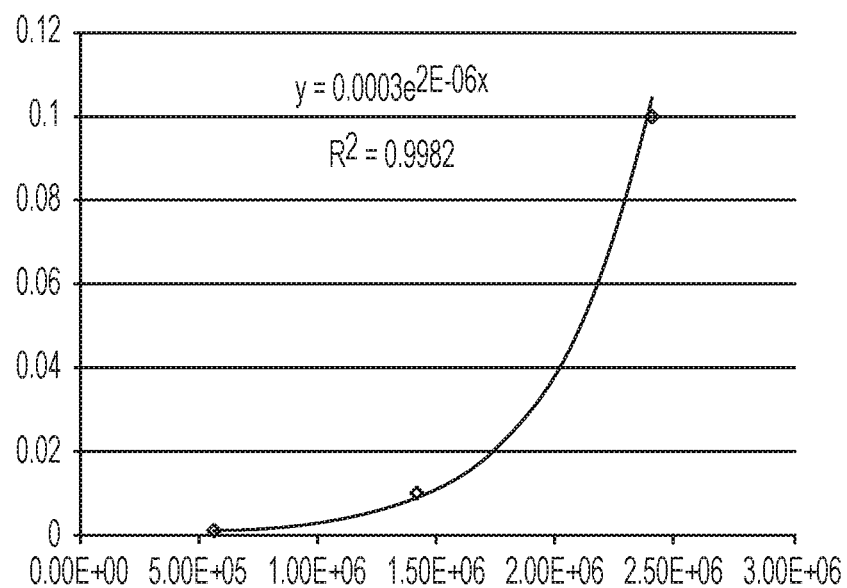
FIG. 2 is a curve illustrating the correlation between the amount of material in a film and the AUC of FIG. 1 obtained according to one embodiment of the invention.

To further explore the relationship between MDPB starting concentration or MDPB amount in the film and the area under the curve, the area was calculated by performing an integration of the curves. A plot of the starting concentration as a function of the area under the curve was plotted as illustrated in FIG. 2. A curve fit was performed on the staring concentration versus AUC data points resulting in a correlation coefficient of $R^2=0.9982$ indicating that the technique can be used to accurately determine mass on a substrate. The curve fit and correlation coefficient are illustrated in FIG. 2.

EXAMPLE 2

Figure 4:
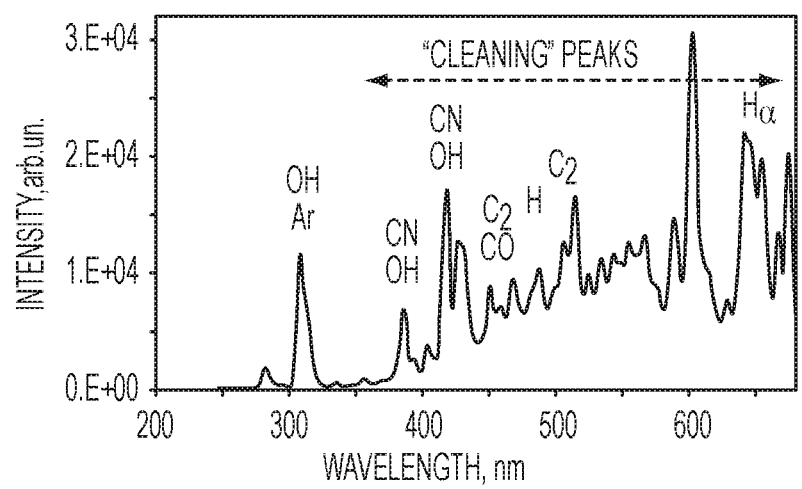
FIG. 4 illustrates an exemplary spectral signature generated during a cleaning step according to an embodiment of the invention.

Coupons of plain titanium alloy foil during cleaning were cleaned with argon plasma at a power of 100 W. The optical emission spectra was recorded. The optical emission spectra obtained after five second of plasma exposure time is illustrated in FIG. 4. The emission peaks were analyzed and possible identifications of the various contaminants were obtained based on correlations between the various elements or molecular fragments and their absorbance at varying wavelengths.

FIG. 4 illustrates the ability of the present invention to produce optical emission spectrum showing the presence of specific contaminants and allowing identification of the various contaminants.

EXAMPLE 3

Three coupons of titanium alloy foil were tested: plain titanium alloy foil, PUL coated titanium, and titanium alloy foil with an adsorbed polymer TPL. Optical emission spectra was generated over a period of one hour of cleaning in argon plasma at a power of 100 W.

Figure 5A:
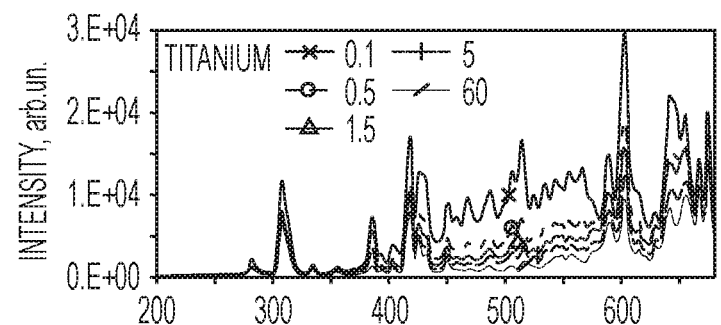
FIGS. 5A-5C illustrate exemplary spectral data used to analyze the thickness of a film according to an embodiment of the invention.

FIG. 5A shows the spectral data for bare titanium and illustrates that a plain titanium alloy foil has surface contaminants that are rapidly removed from the surface since after about 6 to about 30 seconds (0.1 to about 0.5 of a minute), the resultant optical emission spectral data was substantially unchanged.

Figure 5B:
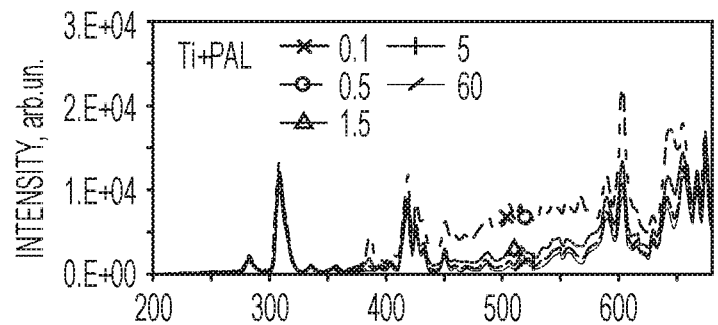

FIG. 5B shows the spectral data for PUL coated titanium and illustrates that it is also cleaned from the surface contaminants rapidly since after about 6 to about 30 seconds (0.1 to about 0.5 of a minute), the resultant optical emission spectral data was substantially unchanged. Without being bound to theory, it is believed that the contaminants are easily cleaned from the sample because PUL was deposited on the surface as a very thin film, arguably as a monolayer about 2 nm to about 5 nm thick.

Figure 5C:
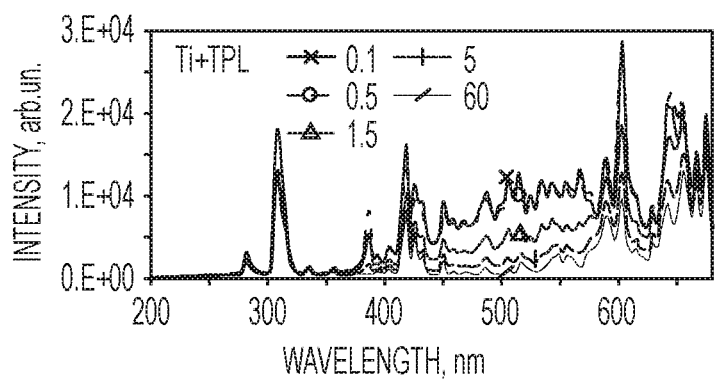

FIG. 5C shows the spectral data for a titanium alloy foil with adsorbed polymer TPL. The adsorbed polymer layer was expected to be much thicker. Indeed, FIG. 5C illustrates that it took significantly longer to remove all of the material, as the optical emissions spectral data kept changing even after 30 seconds to 90 seconds (0.5 to about 1.5 of a minute).

FIGS. 5A through 5C illustrate that there is a correlation the resultant spectral data and the thickness of the film analyzed. The thicker the film, the longer it takes to remove all of the material from it (where removal of all of the material from the film is identified by a steady unchanged spectral data across at least two time points).

EXAMPLE 4

Three samples were tested including: bare titanium, titanium coated with PUL, and titanium with adsorbed with organics such as MDPB. Since MDPB contains Nitrogen, the system was able to detect the presence of CN fragments at 386 nm (as described in example 1) as well as the present of carbon at 419 nm. All three samples were analyzed at two wavelengths, namely: 386 nm and 419 nm, and at two power levels, namely: 25 W and 100 W.

Figure 6A:
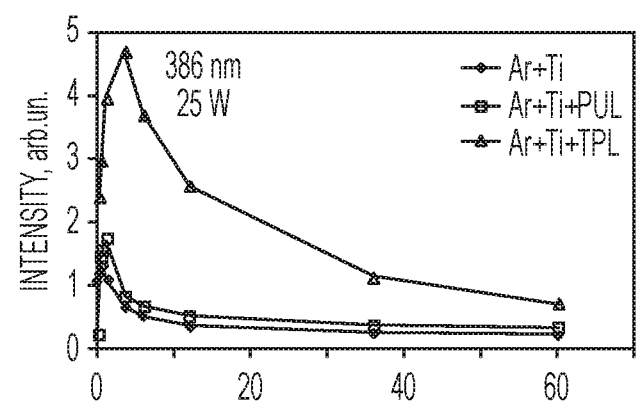
FIGS. 6A-6D illustrate exemplary spectral data used to analyze the presence of an organic monolayer within particular detection parameter according to an embodiment of the invention.

FIG. 6A (386 nm, 25 W) illustrates that similar amounts of CN fragments were present on the bare titanium and the titanium coated with PUL (presumed to have a thin layer of film ranging in thickness from about 2 nm to about 5 nm). FIG. 6A further illustrate that in the sample of titanium adsorbed with organics such as MDPB, the level of CN fragments was elevated when compared to the other two samples. This information has the ability to give atomic identity of the constituents of the film.

Figure 6B:
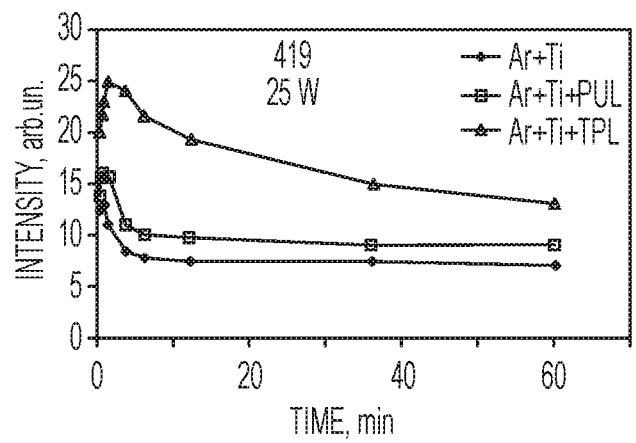

FIG. 6B (419 nm, 25 W) illustrates that there is an increase in total carbon (area under the curve) for the titanium sample adsorbed with organics, particularly when compared to the total carbon detected for bare titanium or for titanium coated with PUL. This shows that analyzing a film according to an embodiment of the invention has the sensitivity to detect a film comprising an organic monolayer on a surface.

Figure 6C:
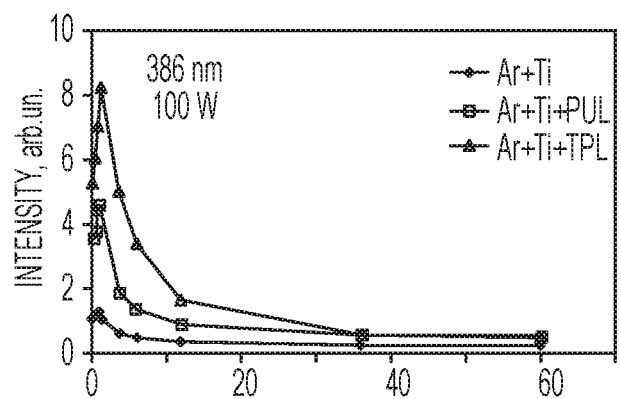
Figure 6D:
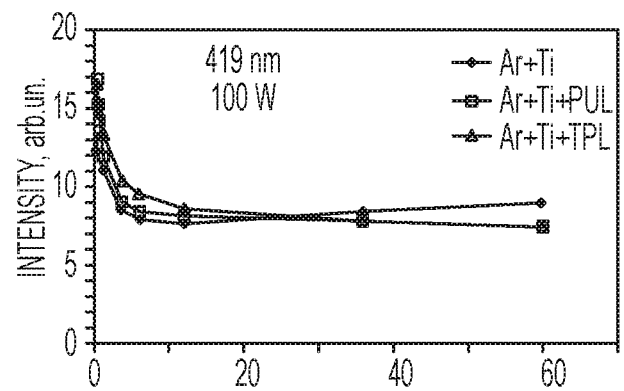

FIGS. 6C (386 nm, 100 W) and 6D (419 nm, 100 W) illustrate somewhat similar patterns to those observed in FIGS. 6A and 6B, although some of the information is lost. Accordingly, in some embodiments, the method of the present invention may be directed to any acceptable RF power level, e.g., up to about 100 W, or an RF ranging between 5 W and 2000 W with variations in the chamber size, vacuum pressure and gas flow rate.

EXAMPLE 5

Surface cleanliness of bare titanium cleaned in plasma was studied using the wet contact analysis (WCA) technique and subsequently the optical emission spectra technique according to an embodiment of the invention.

Figure 7A:
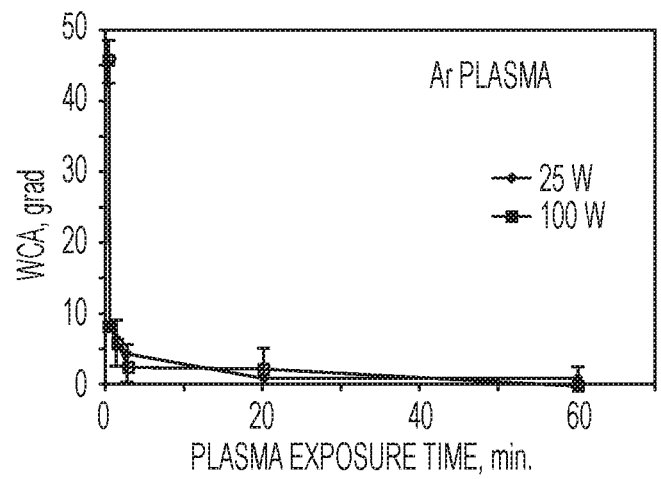
FIGS. 7A-7B illustrate exemplary spectral data comparing the cleanliness analysis of a sample using the wet contact analysis technique and the plasma optical emission spectra technique according to an embodiment of the invention.
Figure 7B:
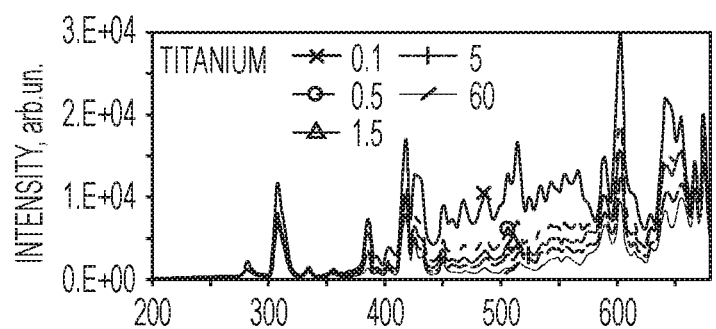

As illustrated in FIG. 7A, after about one minute of cleaning with argon plasma, the analyzed samples achieved a contact angle of about 0, and appeared clean by the WCA technique. However, FIG. 7B illustrates that according to plasma optical emission spectra data, the surface that appeared clean by the WCA technique, still had residual contaminants. Thus, in some embodiments of the present invention, the method of analyzing a film can provide real time cleanliness information with greater sensitivity than other techniques known in the art.

One of ordinary skill in the art would recognize that this method may be used, for example, to determine the type of material present in a film (e.g., based on optimal absorbance at a certain wavelength), and the amount and/or composition of the material present in the film (e.g., based on a predetermined correlation between the area under the curve a sample mass or concentration).

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The term "about", when referring to a physical quantity, is to be understood to include measurement errors within, and inclusive of 2%. For example, "about 100° C." should be understood to mean "100±1° C."

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A method of analyzing a film comprising:
   contacting a film deposited on a substrate with a plasma to produce spectral lines; and
   analyzing the spectral lines,
   wherein the plasma comprises argon plasma, helium plasma, hydrogen plasma or oxygen plasma, and wherein
   the method comprises determining the presence of an element selected from the group consisting of carbon, oxygen, fluorine, nitrogen, phosphorous, chlorine, sulfur, silicon, boron and combinations thereof.

2. The method of claim 1, wherein the film comprises oxide, alkoxide, mixed oxide-alkoxide, phosphonate or organophosphonate.

3. The method of claim 2, wherein the film has a thickness ranging from about 0.001 μm to about 1 μm.

4. The method of claim 2, wherein the substrate is selected from a group consisting of a metal, alloy, polymer, plastic, ceramic, silicon, glass, tissue and fabric.

5. The method of claim 2, wherein the substrate is a medical device.

6. The method of claim 1, wherein the contacting removes one or more materials from the film that produce the spectral lines.

7. The method of claim 6, wherein the removed materials are excited to emit light in the plasma.

8. The method of claim 1, wherein the analyzing is performed with an optical emissions spectrometer.

9. The method of claim 1, comprising determining the amount of material in the film.

10. The method of claim 1, comprising determining the composition of the film.

11. The method of claim 1, comprising determining the presence of an element selected from the group consisting of carbon, oxygen, nitrogen, phosphorus and combinations thereof.

12. The method of claim 1, comprising determining the presence of a molecular fragment selected from the group consisting of C—O, C—N, P—O and combinations thereof.

13. The method of claim 1, wherein the element is selected from the group consisting of fluorine, chlorine, sulfur, silicon, boron and combinations thereof.

14. The method of claim 1, wherein the film is attached to the substrate through covalent bonds.

15. A method of analyzing a film comprising:
placing a film-coated substrate into a chamber;
adding a plasma to the chamber;
recording spectral data produced after addition of the plasma; and
analyzing the spectral data, and wherein
the method comprises determining the presence of an element selected from the group consisting of carbon, oxygen, fluorine, nitrogen, phosphorous, chlorine, sulfur, silicon, boron and combinations thereof.

16. The method of claim 15, further comprising adding an inert gas into the chamber.

17. The method of claim 15, further comprising cleaning the chamber before placing the substrate into the chamber.

18. The method of claim 15, wherein adding the plasma occurs at a pressure ranging from about 0.1 Torr to about 10 Torr.

19. The method of claim 15, wherein adding the plasma occurs at a power ranging from about 1 Watt to about 2,000 Watts.

20. The method of claim 15, wherein analyzing the spectral data comprises analyzing at varying wavelengths, wherein varying wavelengths are associated with varying film components, and wherein the varying film components comprise elements or molecular fragments.

* * * * *